United States Patent [19] [11] 3,985,883
Kathawala [45] Oct. 12, 1976

[54] PYRIDINE CONTAINING PHENOXYPIVALOPHENONE DERIVATIVES
[75] Inventor: Faizulla G. Kathawala, West Orange, N.J.
[73] Assignee: Sandoz, Inc., E. Hanover, N.J.
[22] Filed: Mar. 28, 1975
[21] Appl. No.: 563,160

[52] U.S. Cl. .................. 424/263; 260/294.8 R; 260/295 S; 260/297 R
[51] Int. Cl.² ............... C07D 405/12; A61K 31/44
[58] Field of Search ............ 260/297 R, 294.8 R, 260/295 S; 424/263

[56] References Cited
UNITED STATES PATENTS
3,426,036  2/1969  Biel et al. .................. 260/297 R Primary Examiner—Henry R. Jiles
Assistant Examiner—R. W. Ramsuer
Attorney, Agent, or Firm—Gerald D. Sharkin; Richard E. Vila; Frederick H. Weinfeldt

[57] ABSTRACT
The compounds are cyclic acetals of 4'-(α-hydroxy-α-pyridyl-p-tolyloxy)pivalophenones, and are useful as anti-obesity agents.

17 Claims, No Drawings

PYRIDINE CONTAINING PHENOXYPIVALOPHENONE DERIVATIVES

This invention relates to organic compounds, and more particularly to derivatives of p-tolyloxypivalophenone (and pharmaceutically acceptable acid addition salts thereof) and to pharmaceutical compositions containing such compounds, as well as to the use of such compounds as pharmaceuticals.

The compounds of this invention are conveniently represented by the formula I:

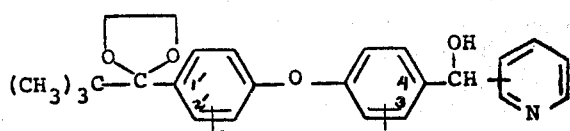

(I)

wherein each of R and R' is, independently, a hydrogen atom, alkyl having from 1 to 4 carbons, e.g., methyl, ethyl, propyl or butyl, including isomers where such exist, or fluoro or chloro, i.e., a halogen atom having an atomic weight of from about 19 to 35; provided that when R is at the 3- position, or R' is at the 2'-position, it is not branched chain alkyl, i.e., that the ring carbon atoms adjacent (ortho) to the 1'- or 4-positions should not bear a branched chain alkyl substituent. The pyridyl radical may be 2-, 3-, or 4-pyridyl.

Compounds I may be obtained by process(a), i.e., by condensing a dioxolane Grignard agent of formula II

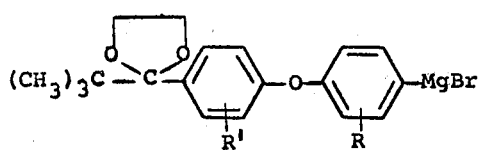

(II)

wherein R and R' are as defined above, with a pyridine carboxaldehyde (III):

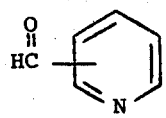

(III)

in the presence of an aprotic solvent and under essentially anhydrous conditions, to obtain a corresponding Grignard adduct, which is then hydrolyzed to the corresponding compound I.

The preparation of a Compound I (process a) is conveniently carried out in the manner, and under the conditions conventionally applied in carrying out the well-known Grignard reactions. Convenient temperatures are those of from about 0° to 70° C, preferably at the reflux temperature of the solvent. Suitable aprotic solvents are ethers, such as tetrahydrofuran and diethyl ether.

The hydrolysis of the resulting adduct to yield a compound I may be carried out in the manner conventionally employed in hydrolyzing Grignard adducts, e.g., by treating the Grignard adduct with water, or an aqueous salt, acid or base, e.g., saturated ammonium chloride solution.

Compounds II, used in process(a), may be obtained in the conventional manner for the preparation of a Grignard reagent (process b); for example, by reacting a compound of the formula IV:

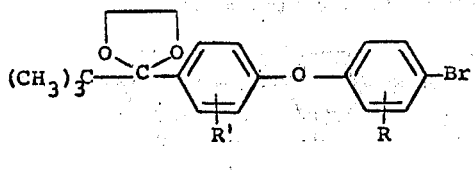

(IV)

wherein R and R' are as defined above, with magnesium metal at temperatures and in a solvent suitable for carrying out process(a), under essentially anhydrous conditions. A small amount of solid iodine may be added to aid in initiating the reaction, as is commonly done in preparing Grignard reagents. Avoidance of moisture to achieve essentially anhydrous conditions as is conventionally practiced in preparing Grignard reagents is exercised, e.g., by employing, "dry" solvents and moisture-free apparatus. It is particularly convenient to prepare Compounds II, in situ, and react directly with Compound III, without recovery.

Compounds IV, used in process(b), are obtainable by ketalization (process c) of corresponding Compounds V:

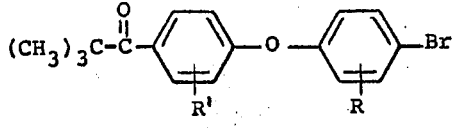

(V)

where R and R' are as defined above.

Process(C) is conveniently conducted by reacting a Compound V with ethylene glycol in the presence of an aromatic sulfonic acid and an inert aromatic solvent at elevated temperatures, e.g., in the range of from about 80° to 140° C, preferably at the reflux temperature of the system, e.g., for a period of time between 12 and 60 hours. Although the particular aromatic sulfonic acid employed is not critical, p-toluene sulfonic acid is preferred. Suitable inert aromatic solvents include benzene, xylene and toluene; the latter being particularly preferred.

Compounds V, used in process(c) are obtainable by brominating (process d) a corresponding p-phenoxypivalophenone of formula VI:

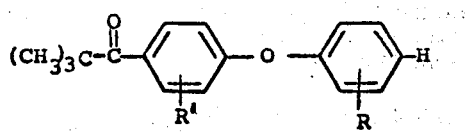

(VI)

wherein R and R' are as defined above.

The bromination (process d) may be carried out by treating a compound VI with molecular bromine in an inert solvent, such as carbon tetrachloride (CCl₄), at moderate temperatures, e.g., from about 0° to 35° C in the presence of a small amount of a Friedel-Crafts reagent, e.g., FeCl₃ as a catalyst.

The compounds of formula VI may be prepared by reacting under Grignard Reaction Conditions, (process e) a compound of the formula VII:

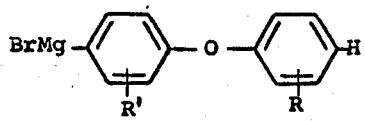

(VII)

in which R and R' are as defined, with trimethylacetyl-chloride, i.e., a compound of the formula VIII:

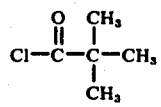 (VIII)

and hydrolyzing the resulting adduct.

Process(e) may conveniently be carried out at temperatures in the range of from about 0° to 100° C, and in the presence of an inert, organic solvent, such as the cyclic and acyclic ethers, such as diethyl ether and tetrahydrofuran. Hydrolysis of the resulting adduct may be carried out in the same manner as described above in connection with process (a). Compounds VII are Grignard reagents and may be prepared from the corresponding p-bromo compounds in the same general manner as described above in connection with process(b).

It will be noted that the Grignard reagents involved in the above-described series of reactions are indicated as magnesium bromides. However, if desired, magnesium iodides may be similarly employed, hence, iodine occurring at each instance where bromine is indicated; bromine, however, is preferred.

The products of the above-described reactions may be recovered and refined in conventional manner, e.g., by crystallization, distillation or chromatographic techniques, such as eluting from a chromatographic column or separating on a silica layer.

Starting materials and reagents used in the above-described reactions, e.g, Compounds III, VI, VII and VIII, are either known and obtained by methods described in the literature, or where not known, may be obtained by methods analogous to those described in the literature. Some of the reactants and starting materials are commercially available.

The above-described series of reactions (process (a) through (e) are conveniently represented in the following Reaction Scheme wherein R and R' are as defined above:

REACTION SCHEME

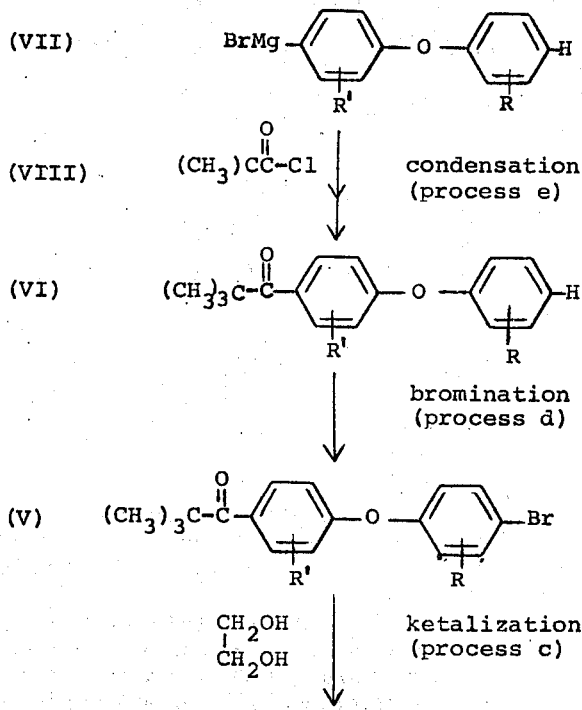

REACTION SCHEME—Continued

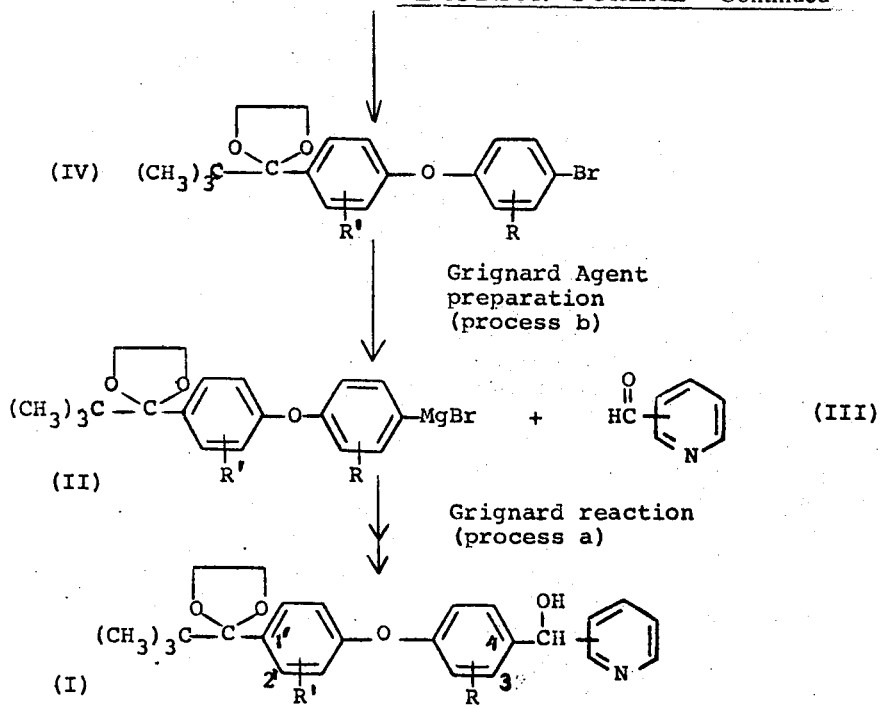

Grignard Agent preparation (process b)

Grignard reaction (process a)

STATEMENT OF UTILITY

The compounds of formula (I) are useful because they possess pharmacological activity in animals, particularly as anti-obesity agents, as indicated by the glucose transport test carried out in Male Wistar rats dosed orally with from about 2 to 200 mg/kg of active material, after at least 20 hours of fasting. One hour after receiving the drug, the animal is sacrificed and the upper small intestine is removed and washed with glucose-saline. A 5 cm section of the intestine is everted so that the mucosal surface is on the outside. One end of the segment is tied off and the center of the sac so formed, is filled with oxygen saturated Kreb's bicarbonate buffer. The other end is then closed to form a sac and the sac is incubated in 10 ml. of oxygen saturated bicarbonate buffer for 60 minutes at 37° C. Both the outside and inside solutions contain initially 0.3% of glucose. At the end of the incubation time the glucose content of the outer(mucosal) and the inner (serosal) solution is determined using the standard Autoanalyzer procedure. Similar preparations are prepared simultaneously from animals receiving the vehicle only to serve as controls. The percent inhibition of glucose transport caused by the drug is calculated from the formula $$\% I = 100 - \left(\frac{S_t - M_t}{S_c - M_c} \times 100\right)$$

where
$I$ equals inhibition
$S$ equals glucose concentration (mg%) of serosal fluid at the end of an expirment
$M$ equals glucose concentration (mg%) of mucosal fluid at the end of an experiment
$c$ equals control animal
$t$ equals drug treated animal.
For such usage, the compounds (I) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups and elixirs and parenterally as solutions, suspensions, dispersions, emulsions and the like, e.g., a sterile injectable aqueous formulation. The dosage will vary depending upon the mode of administration utilized and the particular compound employed.

The compounds of formula (I) may be similarly administered in the form of their non-toxic pharmaceutically acceptable salts. Such salts possess the same order of activity as the free base, and are readily prepared by reacting the base with an appropriate acid and, accordingly, are included within the scope of this invention. Representative of such salts are the mineral acid salts, such as the hydrochloride, hydrobromide, sulfate, phosphate and the like and the organic acid salts such as succinate, benzoate, acetate, p-toluenesulfonate, benzene-sulfonate and the like.

The anti-obesity effective dosage of compounds (I) employed in the alleviation of obesity will vary depending on the particular compound employed and the severity of the condition being treated. However, in general, satisfactory results are obtained when the compounds of formula (I) are orally administered at a daily dosage of from about 2 to about 200 milligrams per kilogram of animal body weight, preferably given in divided doses two to four times per day, or in sustained release form. For most large mammals, the total daily dosage is from about 150 milligrams to about 1500 milligrams. Dosage forms suitable for internal use comprise from about 37.5 to about 750 milligrams of active compound in intimate admixture with a solid or liquid pharmaceutically acceptable carrier or diluent. In general, oral administration is preferred. Solid compositions, e.g., capsules and tablets, are most preferred.

A representative formulation suitable for oral administration 2 to 4 times a day for the treatment of obesity is a capsule prepared by standard encapsulating techniques which contain the following:

| Ingredients | Weight (mg) |
| --- | --- |
| 4'-(α-hydroxy-α-[4-pyridyl]-p-tolyloxy) pivalophenone, cyclic ethylene acetal. | 100 |
| inert solid diluent (starch, lactose, kaolin) | 200 |

In the following examples, which are illustrative of the invention, temperatures are in degrees centigrade, and room temperature is 20° to 30° C, unless indicated otherwise.

The compounds I having a 3-pyridyl or 4-pyridyl radical are generally preferred, and the particularly preferred compounds I are those having a 4-pyridyl radical. Compounds I wherein each of R and R' is a hydrogen atom, e.g., the product of Example 1, are also generally preferred.

EXAMPLE 1

4'-(α-hydroxy-α-[3-pyridyl]-p-tolyloxy)pivalophenone, cyclic ethylene acetal.

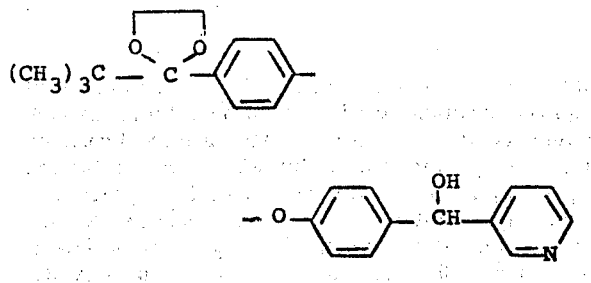

Step A: Preparation of p-phenoxy-pivalophenone (a compound VI)

To a flask containing 33.6 g. of magnesium and a few crystals of iodine, is added 50 to 70 ml. of a solution of 300 g. of 4-bromodiphenyl ether in 500 ml. of absolute tetrahydrofuran. The remainder of the solution is added as needed to maintain a gentle reflux and the resulting mixture heated to reflux for 30 minutes. The resulting mixture is then added to a solution of trimethylacetyl chloride in 500 ml. of absolute tetrahydrofuran at a rate so as to maintain a temperature of from 40° to 50° C. The resulting mixture is then stirred at ambient temperature for 1 hour. 200 ml. of 2N. hydrochloric acid is then added. The organic layer is washed twice with 1 liter of 2N. sodium carbonate solution, dried and evaporated in vacuo to a liquid. The liquid thus obtained is distilled under reduced pressure to obtain p-phenoxypivalophenone, b.p. 136°–139° C. at 0.1 mm/Hg.

Step B: Preparation of p-bromophenoxypivalophenone (a compound V)

To a solution of 100 g. of p-phenoxypivalophenone in 2 l. of carbontetrachloride is added 5 g. ferric chloride and then dropwise a solution of 64 g. bromine in 100 ml. carbon tetrachloride over a period of 1 hour. The mixture is stirred at room temperature for 3 days; thereafter the organic phase is extracted three times with saturated aqueous sodium sulfite solution, washed with water, dried over sodium sulfate (anhydrous), filtered and evaporated in vacuo to dryness to yield a clear oil. The clear oil is crystallized from pentane to give p-bromophenoxypivalophenone, m.p. 73°–74° C.

Step c: Preparation of 2-(t.-butyl)-2-4-(4'-bromophenoxyphenyl)1,3-dioxolane (a compound IV).

A mixture of 100 g. of p-bromophenoxypivalophenone, 100 ml. ethylene glycol and 1.5 g. p-toluenesulfonic acid in 1500 ml. toluene is refluxed with a Dean-Stark trap for 48 hours to remove water formed in the reaction. The resultant toluene solution is extracted several times with 10% sodium bicarbonate solution, washed with water, dried over potassium carbonate (anhydrous), filtered and evaporated in vacuo to dryness to give a residue. From the residue is crystallized with pentane, the title bromo-product, m.p. 84°–86° C.

Step D: Preparation of 4'-(α-hydroxy-α-[3-pyridyl]-p-tolyloxy)-pivalophenone, cyclic ethylene acetal (a compound I).

To 2.8 g. of magnesium turnings and a trace of iodine is added a solution of 37.7 g. 2-(t-butyl)-2-4-(4'-bromophenoxyphenyl)1,3-dioxolane in 100 ml. absolute tetrahydrofuran. The Grignard solution is refluxed for 2 hours to insure complete reaction. A solution of 11 g. 3-pyridine carboxaldehyde in 50 ml. absolute tetrahydrofuran is then added dropwise and the reaction mixture stirred at room temperature for 16 hours. Thereafter 300 ml. of saturated aqueous ammonium chloride solution is added, the organic layer separated, washed well with water, dried over sodium sulfate (anhydrous), filtered and evaporated on silica gel column, eluting with chloroform/methanol (98:2), to obtain the title product, m.p. 109°–111° C.

EXAMPLE 2

Following the procedure of Example 1, but using in place of the 4-bromodiphenyl ether used in Step A, thereof, an equivalent amount of:
a. 1-bromo-4-(m-toloxy)-benzene;
b. 1-bromo-4-(o-fluorophenoxy)-benzene;
c. 1-bromo-4-(m-chlorophenoxy)-benzene;
d. 1-bromo-4-(o-toloxy)-3-chlorobenzene;
e. 1-bromo-4-(o-ethylphenoxy)-2-chlorobenzene;
f. 5-bromo-2-phenoxytoluene;
g. 1-bromo-4-(m-chlorophenoxy)-3-chlorobenzene;
h. 1-bromo-4-(o-chlorophenoxy)-benzene; and
i. 1-bromo-4-phenoxy-2-chlorobenzene;
there is similarly obtained as final product:
a. 4'-(α-hydroxy-α-[3-pyridyl]-3-methyl-p-tolyoxy)-pivalophenone, cyclic ethylene acetal;
b. 4'-(α-hydroxy-α-[3-pyridyl]-2-fluoro-p-tolyloxy)-pivalophenone, cyclic ethylene acetal;
c. 4'-(α-hydroxy-α-[3-pyridyl]-3-chloro-p-tolyloxy)-pivalophenone, cyclic ethylene acetal;
d. 3'-chloro-4'-(α-hydroxy-α-[3-pyridyl]-2-methyl-p-tolyloxy)-pivalophenone, cyclic ethylene acetal;
e. 2'-chloro-4'-(α-hydroxy-α-[3-pyridyl]-2-ethyl-p-tolyloxy)-pivalophenone, cyclic ethylene acetal;
f. 3'-methyl-4'-(α-hydroxy-α-[3-pyridyl]-p-tolyloxy)-pivalophenone, cyclic ethylene acetyl;
g. 3'-chloro-4'-(α-hydroxy-α-[3-pyridyl]-3-chloro-p-tolyloxy)-pivalophenone, cyclic ethylene acetal;
h. 4'-(α-hydroxy-α-[3-pyridyl]-2-chloro-p-tolyloxy)-pivalophenone, cyclic ethylene acetal; and i. 2'-chloro-4'-(α-hydroxy-α-[3-pyridyl]-p-tolyloxy)-pivalophenone, cyclic ethylene acetal.

EXAMPLE 3

Following the procedure of Example 1, but replacing the 3-pyridine carboxaldehyde used in Step D thereof, with a. 2-pyridine carboxaldehyde; or
b. 4-pyridine carboxaldehyde;

there is similarly obtained the cyclic ethylene acetals of:

a. 4'-(α-hydroxy-α-[2-pyridyl]-p-tolyloxy)-pivalophonone, m.p. 46°–48° C.; and
b. 4'-(α-hydroxy-α-[4-pyridyl]-p-tolyloxy)-pivalophenone, m.p. 128°–130° C.

What is claimed is:

1. A compound which is an acetal of the formula

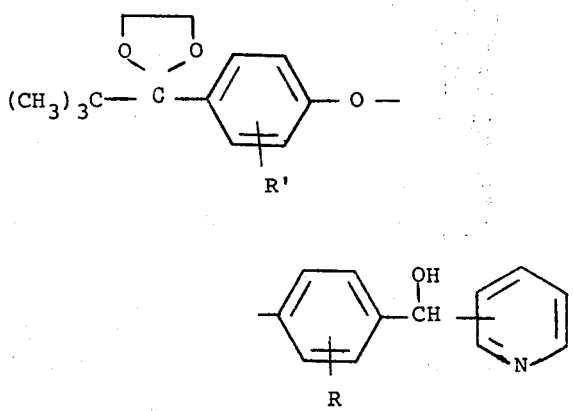

wherein each of R and R' is, independently, a hydrogen atom, alkyl having from 1 to 4 carbons, or a halogen atom having an atomic weight of from about 19 to 35, provided that when any of R is at the 3 [2]-position, or R' is at the 2'-position, it is not branched chain alkyl, or a pharmaceutically acceptable acid addition salt thereof.

2. A compound of claim 1 in which the pyridyl radical is 2-pyridyl.

3. A compound of claim 2 in which each of R and R' is a hydrogen atom.

4. The compound of claim 3 which is 4'-(α-hydroxy-α-[2-pyridyl]-p-tolyloxy)-pivalophenone, cyclic ethylene acetal.

5. A compound of claim 1 in which the pyridyl radical is 3-pyridyl.

6. A compound of claim 5 in which each of R and R' is a hydrogen atom.

7. The compound of claim 6 which is 4'-(α-hydroxy-α-[3-pyridyl]-p-tolyloxy)pivalophenone, cyclic ethylene acetal.

8. A compound of claim 1 in which the pyridyl radical is 4-pyridyl.

9. A compound of claim 8 in which each of R and R' is a hydrogen atom.

10. The compound of claim 9 which is 4'(α-hydroxy-α-[4-pyridyl]-p-tolyloxy)-pivalophenone, cyclic ethylene acetal.

11. A pharmaceutical composition for treatment of obesity comprising as active ingredient an anti-obesity effective amount of a compound of claim 1 and a pharmaceutically acceptable carrier.

12. A composition of claim 11 in which the compound is present in an amount of from about 37.5 to 750 milligrams.

13. A composition of claim 11 in which the carrier is solid.

14. A method of treating obesity in a mammal, by administering to said mammal an amount of a compound of claim 1, effective in treating obesity in said mammal.

15. A method of claim 14 in which the compound is administered orally.

16. A method of claim 14 in which the amount of the compound administered daily is from about 150 to 1500 milligrams.

17. A method of claim 14 in which the amount of the compound administered daily is from about 2 to 200 milligrams per kilogram of animal body weight.

* * * * *